United States Patent [19]
Crosby et al.

[11] Patent Number: 6,110,729
[45] Date of Patent: Aug. 29, 2000

[54] ENZYMATIC PROCESS FOR STEREOSELECTIVE PREPARATION OF A TERTIARY ALCOHOL BY HYDROLYSIS OF CORRESPONDING ACID

[75] Inventors: John Crosby; John David Pittam, both of Macclesfield; Robert Antony Holt, Billingham, all of United Kingdom

[73] Assignee: Zeneca Limited, United Kingdom

[21] Appl. No.: 09/171,039

[22] PCT Filed: Apr. 7, 1997

[86] PCT No.: PCT/GB97/00965

§ 371 Date: Oct. 9, 1998

§ 102(e) Date: Oct. 9, 1998

[87] PCT Pub. No.: WO97/38124

PCT Pub. Date: Oct. 16, 1997

[30] Foreign Application Priority Data

Apr. 10, 1996 [GB] United Kingdom .................. 9607458

[51] Int. Cl.$^7$ ................................ C07C 1/04; C07F 1/04
[52] U.S. Cl. ............................................................ 435/280
[58] Field of Search .............................................. 435/280

[56] References Cited

U.S. PATENT DOCUMENTS

| | | |
|---|---|---|
| 2,541,466 | 2/1951 | Dickey . |
| 4,929,760 | 5/1990 | Kitazume et al. . |
| 5,272,163 | 12/1993 | Russell et al. . |
| 5,334,534 | 8/1994 | Chen . |
| 5,382,598 | 1/1995 | Russell et al. . |

FOREIGN PATENT DOCUMENTS

| | | |
|---|---|---|
| 0 213 393 | 3/1987 | European Pat. Off. . |
| 0 459 455 A2 | 12/1991 | European Pat. Off. . |
| 0 524 781 | 1/1993 | European Pat. Off. . |
| 0 566 485 A2 | 10/1993 | European Pat. Off. . |
| 2 241 953A | 9/1991 | United Kingdom . |
| WO 84 04543 | 11/1984 | WIPO . |
| WO 94 20633 | 9/1994 | WIPO . |
| WO 94 26739 | 11/1994 | WIPO . |
| WO 95 01450 | 1/1995 | WIPO . |
| WO 95 03421 | 2/1995 | WIPO . |
| WO 95 12573 | 5/1995 | WIPO . |

OTHER PUBLICATIONS

Pichika Ramaiah et al., "Direct Trifluoromethylation of α–Keto Esters to β,β,β–Triflurolactic Acid Derivatives Using Trifluoromethyltrimethylsilane", SYNLETT, vol. 9, pp. 643–644 (1991).

Tomoya Kitatsume et al., "Enzymic manufacture of optically active fluorinated alcohols", Chemical Abstracts, vol. 116, No. 12, Abstract No. 127023, p. 718 (1992).

F. Yasuhara et al., "Gas chromatographic separation of enantiomeric amino acids and amines with α–methoxy–α–trifluoromethylpropionic acid as a chiral derivatizing agent", Journal of Chromatography A, 694, pp. 227–236, (1995) Elsevier Science B.V.

Marie da Graca Nascimento et al., "Enzyme–Catalyzed esterifications in Microemulsion–based Organo Gels", Tetrahedron Letters, vol. 33, No. 40, pp. 5891–5894 (1992).

R. A. Darrall et al., "516. Organic Fluorides. Part IX The Formation and Resolution of α–Hydroxy–α–trifluoromethylpropionic Acid", J. Chem. Soc., pp. 2329–2332 (1951).

Marc Tordeux et al., "Reactions of Trifluoromethyl Bromide and Related Halides: Part 9. Comparison between Additions to Carbonyl Compounds, Enamines, and Sulphur Dioxide in the Presence of Zinc", J. Chem. Soc. Perkin Trans. 1, pp. 1951–1957 (1990).

Markus Gautschi et al., "Synthesis of (R)– and (S)–2–tert–Butyl–6–trifluoromethyl–1,3–dioxin–4–ones, Transformations into 3–Hydroxy–3–(trifluoromethyl)alkanoates, and Surprising Differences in the Reactivity of $CH_3$– and $CF_3$–Substituted Compounds", Angew. Chem. Int. Ed. Engl., 31, No. 8, pp. 1083–1085 (1992).

Ian Brackenridge et al., "Enzymatic Resolution of Oxalate Esters of a Tertiary Alcohol Using Porcine Pancreatic Lipase", J. Chem. Soc. Perkin Trans. 1, pp. 1093–1094 (1993).

Beat Weber et al., "Enantiomerically Pure Tertiary Alcohols by Taddol–Assisted Additions to Ketones—or How to Make a Grignard Reagent Enantioselective", Angew. Chem. Int. Ed. Eng., 31, No. 1, pp. 84–86 (1992).

John F. Coope et al., "Biocatalytic Resolution of a Tertiary Quinuclidinol Ester Using Pig Liver Esterase", Tetrahedron: Asymmetry, vol. 6, No. 6, pp. 1393–1398 (1995) Elsevier Science Ltd.

David O'Hagan et al., "The Resolution of Tertiary α–Acetylene–Acetate Esters by the Lipase from Candida Cylindracea", Tetrahedron: Asymmetry, vol. 5, No. 6, pp. 1111–1118 (1994) Elsevier Science Ltd.

Arthur J. Roth, "1,1,1–Trihalo–2–cyano–2–acetoxypropane", Chemical Abstracts, vol. 61, Col. 4228 (1964).

Charles Heidelberger, "5–Trifluoromethyluracil and derivatives", Chemical Abstracts, vol. 63, Col. 10447 (1965).

Charles Heidelberger et al., "Syntheses of 5–trifluoromethyluracil and 5–trifluromethyl–2'–deoxyuridine", Chemical Abstracts, vol. 60, Col. 5620, p. 5620 (1964).

Joseph B. Dickey, "α–(Fluromethyl)acrylonitriles", Chemical Abstracts, vol. 45, Col. 5716 (1951).

Primary Examiner—Sandra E. Saucier
Attorney, Agent, or Firm—Kenneth F. Mitchell

[57] ABSTRACT

A stereoselective method for making compounds of Formula VIII

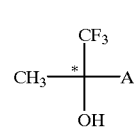

wherein A and * are as defined in the specification. Enzymic processes and intermediates useful for preparing compound of Formula VIII are disclosed.

7 Claims, No Drawings

ENZYMATIC PROCESS FOR STEREOSELECTIVE PREPARATION OF A TERTIARY ALCOHOL BY HYDROLYSIS OF CORRESPONDING ACID

FIELD OF THE INVENTION

The present invention relates to methods of synthesizing pharmaceutical compounds and intermediates used in the synthesis of such chemical compounds. In particular the present invention relates to novel enzymatic processes for stereoselective preparation of N-aryl or -pyridyl propanamides having a tertiary alcohol stereogenic center, and enantiomeric intermediates useful for the synthesis of such compounds.

BACKGROUND OF THE INVENTION

N-(4-benzoylphenyl)-3,3,3-trifluoro-2-hydroxy-2-methylpropanamide and other N-aryl or -pyridyl propanamides are disclosed in U.S. Pat. No. 5,272,163 which issued Dec. 21, 1993 to Russell et al. Such compounds are cellular potassium channel openers and are thus usefull in the treatment of urinary incontinence and other diseases and conditions including hypertension, asthma, peripheral vascular disease and angina, as disclosed in the aforementioned patent. U.S. Pat. No. 5,272,163 also discloses a method of preparing the (S)-(−) enantiomer of N-(4-benzoylphenyl)-3,3,3-trifluoro-2-hydroxy-2-methylpropanamide which method employs diastereomeric ester formation followed by chromatographic separation, and subsequent removal of the ester group by treatment with a base.

SUMMARY OF THE INVENTION

The present invention provides novel enzymatic process for stereoselective preparation of N-aryl or -pyridyl propanamides having a tertiary alcohol stereogenic center, as exemplified by the preparation of (S)-(−)-N-(4-benzoylphenyl)-3,3,3-trifluoro-2-hydroxy-2-methylpropanamide. Such compounds are cellular potassium channel openers and are thus useful in the treatment of urinary incontinence and other diseases and conditions including hypertension, asthma, peripheral vascular disease and angina.

The novel methods of the invention employ an enzymatic step to selectively cleave an ester group from one enantiomer of a racemic mixture of esters formed from the N-aryl or pyridylpropanamide. The enzymatic step can be followed by separation of the remaining ester from the alcohol so produced. The recovered ester that was not cleaved in the enzymatic step can be hydrolyzed if desired to produce the corresponding alcohol.

The present invention also provides methods for synthesizing intermediates useful in the synthesis of the aforementioned N-aryl or -pyridylpropanamides, as exemplified by the preparation of (S)-3,3,3-trifluoro-2-hydroxy-2-methylpropanoic acid useful in the preparation of (S)-(−)-N-(4-benzoylphenyl)-3,3,3-trifluoro-2-hydroxy-2-methylpropanamide.

Methods for stereoselective synthesis of N-aryl or -pyridyl propanamides having a tertiary alcohol stereogenic center, exemplified by (S)-(−)-N-(4-benzoylphenyl)-3,3,3-trifluoro-2-hydroxy-2-methylpropanamide, and intermediates useful in the synthesis of such compounds are provided herein.

These and other aspects of the present invention as set forth in the appended claims are described in their preferred embodiments in the following detailed description of the invention.

DETAILED DESCRIPTION OF THE INVENTION

A first aspect of the invention provides a method of preparing an optically active compound of Formula I

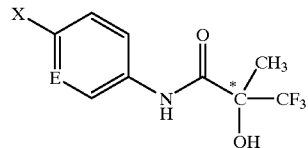

wherein E is selected from nitrogen and CZ wherein C is a ring carbon and Z is a substituent defined below, wherein:
when E is CZ, X and Z are selected from the group consisting of:
(A) X is ArY wherein Y is a linking group selected from carbonyl, sulfinyl, and sulfonyl and Ar is selected from the group consisting of:
phenyl substituted with 0–2 substituents selected from halo, hydroxy, cyano, $C_1$–$C_4$ alkyl, and $C_1$–$C_4$ alkoxy;
six-membered heteroaryl rings containing 1–2 nitrogen atoms as the only heteroatoms;
five-membered heteroaryl rings containing from 1–2 heteroatoms selected from nitrogen, oxygen, and sulfur; and
Z is selected from hydrogen, cyano, halo, hydroxy, $C_1$–$C_4$alkyl, and $C_1$–$C_4$alkoxy; and
(B) X is cyano and Z is selected from the group consisting of phenylthio, phenylsulfinyl. and phenylsulfonyl the phenyl rings of which are substituted with 0–2 substituents selected from halo, hydroxy, cyano, nitro, $C_1$–$C_4$alkyl, and $C_1$–$C_4$alkoxy; and
when E is nitrogen, X is independently selected from any of the values for X given above in (A);
and * is an optically active chiral center,
comprising the step of treating a racemic compound of Formula II with a hydrolase enzyme. The compounds of Formula II are defined as follows:

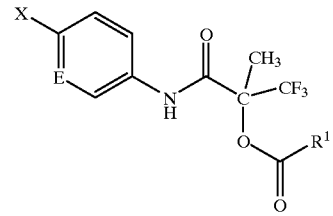

Formula II wherein E and X have the meanings previously defined herein; and
$R^1$ is alkyl optionally substituted by one or more substituents independently selected from hydroxy, halogen, $C_1$–$C_4$ alkoxy, cyano, $C_1$–$C_4$ alkylamino and $C_1$–$C_4$ dialkylamino. Preferably, $R^1$ is optionally substituted $C_1$–$C_7$ alkyl, more preferably optionally substituted $C_1$–$C_5$ alkyl. A preferred substituent is halogen, more preferably chloro. In the method of the invention, the hydrolase enzyme cleaves the ester group from one enantiomer of the ester of Formula II to provide the (S) or (R) enantiomer as the alcohol of Formula I, depending on the specificity of the enzyme, and leaving the other enantiomer in the unreacted substrate.

The method of the invention can also comprise the step of separating the product formed during the enzymatic step from the unreacted starting material, i.e. separating the alcohol of Formula I formed during the enzymatic treatment and the unreacted ester starting compound of Formula II. The enzyme selectively cleaves the ester group from one enantioner of the racemic mixture of the compound of Formula II to produce the alcohol. The compound of Formula I and the unreacted ester starting material of Formula II can be separated using conventional methods such as chromatography on a silica column. When the desired enantiomer is the unreacted ester, the method of the invention can further comprise converting the ester to the corresponding alcohol. The ester can be converted to the corresponding alcohol by treatment with a base such as sodium hydroxide.

A preferred embodiment of this aspect of the invention provides a method for preparing (S)-(−)-N-(4-benzoylphenyl)-3,3,3-trifluoro-2-hydroxy-2-methyl propanamide (Formula I wherein * is the (S) configuration, E is CZ, X is ArY, Y is carbonyl, Ar is phenyl, and Z is hydrogen).

Racemic N-(4-benzoylphenyl)-3,3,3-trifluoro-2-hydroxy-2-methylpropanamide can be converted to an ester using conventional methods known in the art. For example, the racemic compound is reacted with an acid chloride of Formula III:

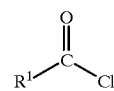

Formula III wherein $R^1$ has the meaning defined hereinabove, in the presence of a base such as triethylamine, as shown in Scheme 1. Preferred compounds of Formula III include monochloroacetyl chloride and butyryl chloride. Racemic N-(4-benzoylphenyl)-3,3,3-trifluoro-2-hydroxy-2-methylpropanamide can be prepared, for example, using the method of U.S. Pat. No. 5,382,598 or the method described herein.

The resulting ester derived from N-(4-benzoylphenyl)-3,3,3-trifluoro-2-hydroxy-2-methylpropanamide is then reacted with a hydrolase enzyme, preferably a lipase, more preferably crude porcine pancreatic lipase, which selectively cleaves the ester group from the (R) enantiomer, leaving the ester of the (S) enantiomer. The reaction preferably takes place in a buffered aqueous solution at approximately pH 7 with tert-butyl methyl ether (MTBE) as cosolvent. However, it is to be understood that the pH of the buffered aqueous solution will depend on the enzyme employed in the reaction. The presence of the cosolvent in the reaction mixture is optional. The reaction is allowed to proceed until available substrate is reacted, which may be from about one to about three days. The reaction may proceed faster or slower depending on the enzyme used and the reaction conditions. It may also be possible, using an enzyme with the opposite specificity, to cleave the ester group from the (S) enantiomer directly in the enzymatic step.

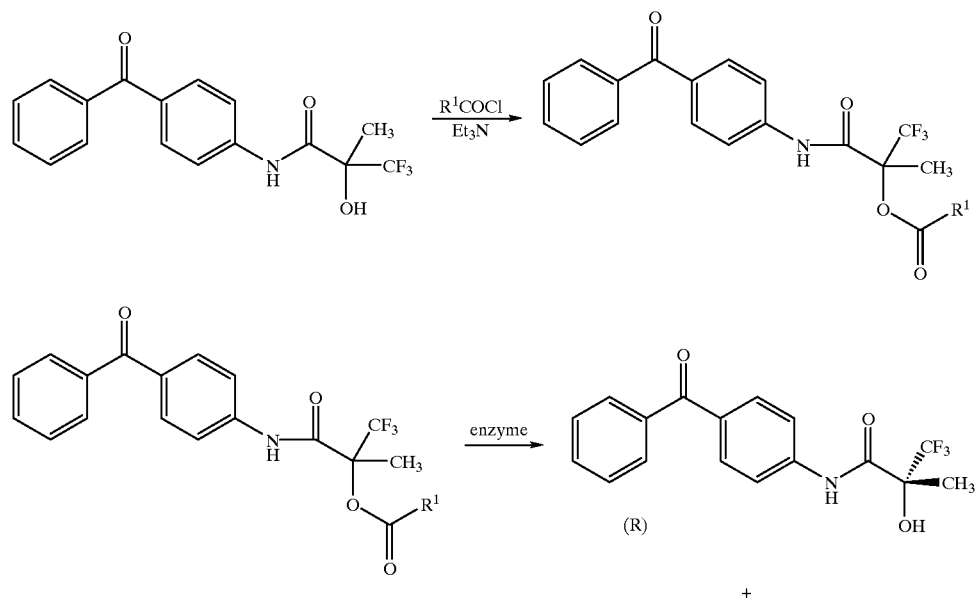

Scheme 1

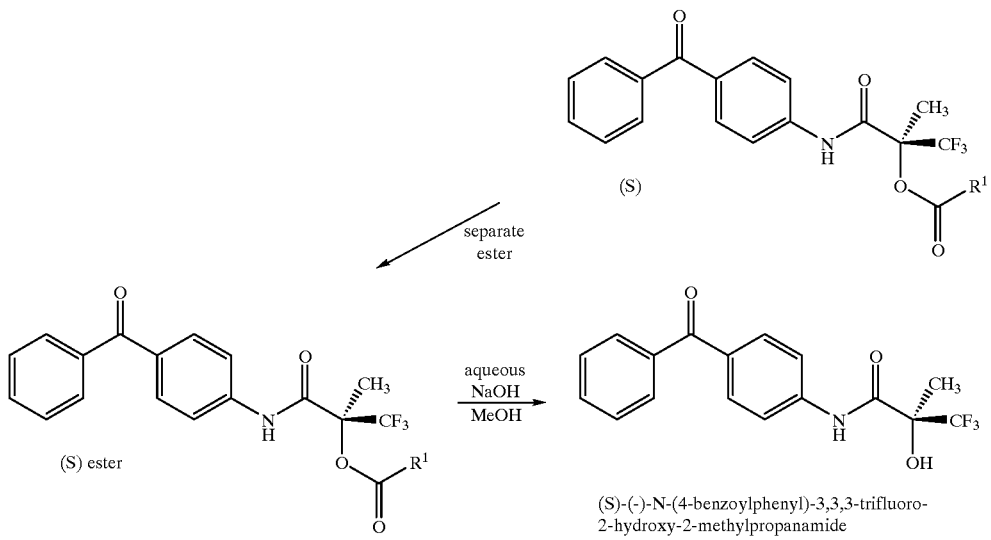

The (S) ester may be separated from the (R) enantiomer of N-(4-benzoylphenyl)-3,3,3-trifluoro-2-hydroxy-2-methylpropanamide by standard methods such as chromatography on a silica column or by any other suitable method. Where the ester is the (S) enantiomer, it is then treated with a base such as sodium hydroxide in aqueous-methanol or other solvent to remove the ester group and provide (S)-(−)-N-(4-benzoylphenyl)-3,3,3-trifluoro-2-hydroxy-2-methylpropanamide.

This aspect of the present invention has been exemplified by synthesis of (S)-(−)-N-(4-benzoylphenyl)-3,3,3-trifluoro-2-hydroxy-2-methylpropanamide. Other N-aryl or -pyridyl propanamides of Formula I can be prepared by substituting racemic mixtures of such compounds for N-(4-benzoylphenyl)-3,3,3-trifluoro-2-hydroxy-2-methylpropanamide in the method described in Scheme 1. The use of protecting groups may be needed for some substituents. Racemic mixtures of compounds of Formula I can be prepared in accordance with the methods of U.S. Pat. No. 5,382,598.

Scheme 2 shows the preparation of (S)-(−)-N-(4-benzoylphenyl)-3,3,3-trifluoro-2-hydroxy-2-methylpropanamide wherein the (S)-3,3,3-trifluoro-2-hydroxy-2-methylpropanoic acid intermediate is prepared by selective crystallization with a resolving agent rather than by an enzymatic process. As shown in Scheme 2, 1,1,1-trifluoroacetone (1) is reacted with a cyanide such as sodium cyanide in the presence of an acid such as hydrochloric acid to form racemic 3,3,3-trifluoro-2-hydroxy-2-methylpropanenitrile (2). The racemic 3,3,3-trifluoro-2-hydroxy-2-methylpropanenitrile (2) is then hydrolyzed with, for example, hydrochloric acid or sulfuric acid to provide racemic 3,3,3-trifluoro-2-hydroxy-2-methylpropanoic acid (3). Racemic (3) is then selectively crystallized with a resolving agent such as (1R,2S)-norephedrine (4) to form a salt (5) which may be recrystallized to diastereomeric purity. The purified salt (6) contains (S)-3,3,3-trifluoro-2-hydroxy-2-methylpropanoic acid (7). (S)-3,3,3-Trifluoro-2-hydroxy-2-methylpropanoic acid (7) after liberation from the salt is reacted with 4-aminobenzophenone (8) and SOCl$_2$ using an organic base such as triethylamine or Hunig's base to form (S)-(−)-N-(4-benzoylphenyl)-3,3,3-trifluoro-2-hydroxy-2-methylpropanamide (9), which can then be purified by recrystallization.

For preparation of other N-aryl or -pyridyl propanamides of Formula I which have the S configuration, an amine of Formula IV as defined hereinbelow is substituted for 4-aminobenzophenone (8) in the synthesis shown in Scheme 2. The amine is reacted with

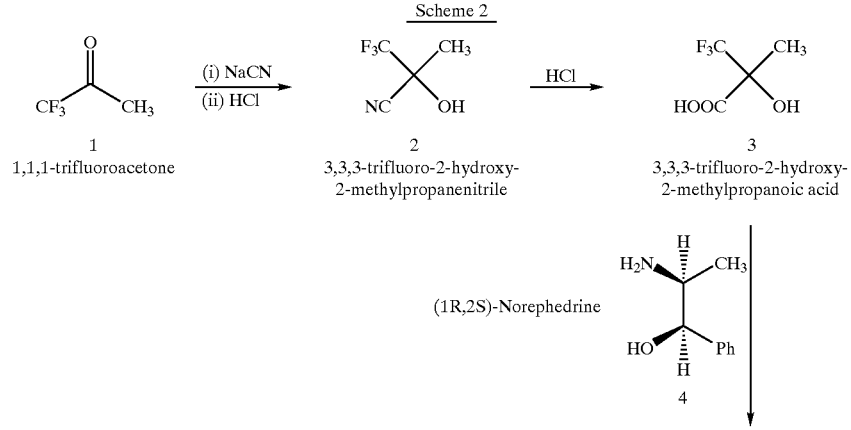

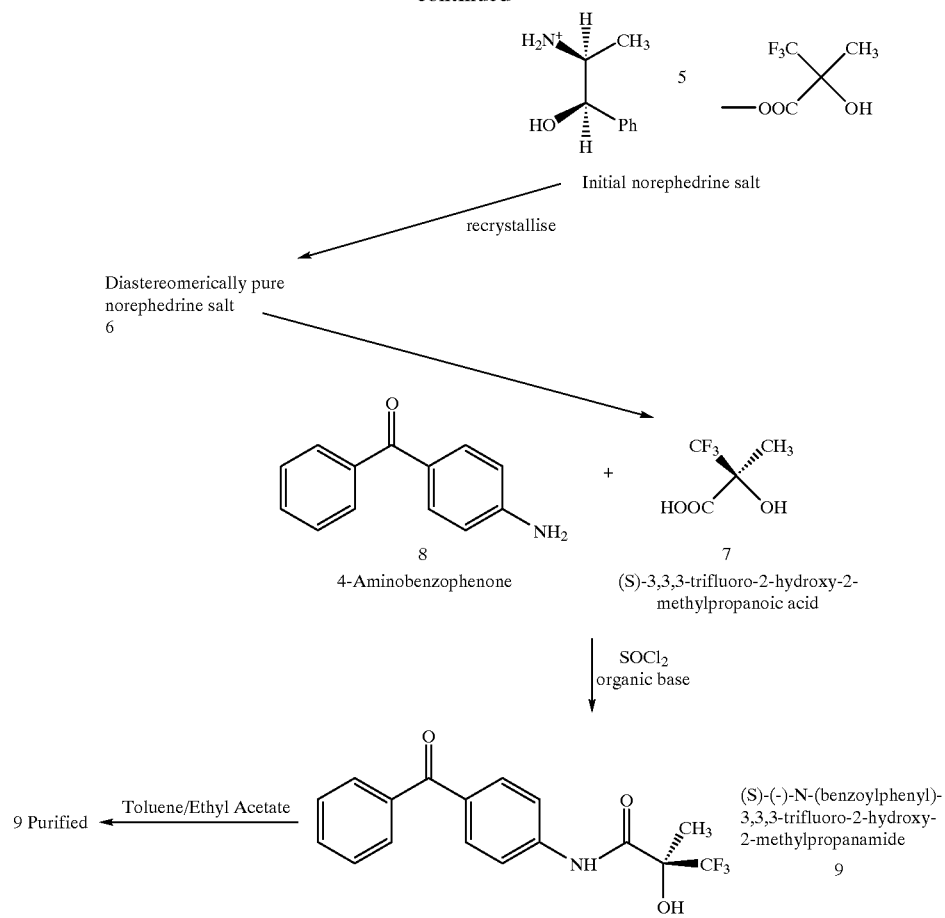

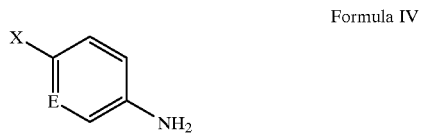

(S)-3,3,3-trifluoro-2-hydroxy-2-methylpropanoic acid in a like manner to produce the amide product which can then optionally be purified by conventional methods. Amines of Formula IV are also described in the U.S. Pat. No. 5,272,163.

The compounds of Formula IV are defined as follows:

Formula IV wherein X and E have the meanings defined hereinabove. Such amines of Formula IV can be prepared according to the methods disclosed in U.S. Pat. No. 5,272,163.

In addition to the method shown in Scheme 2, the coupling of a compound of Formula IV with (S)-3,3,3-trifluoro-2-hydroxy-2-methylpropanoic acid can be conducted in other suitable solvents and in the presence of other suitable coupling reagents. Suitable coupling reagents generally known in the art as standard peptide coupling reagents can be employed, for example thionyl chloride (see Morris et al., J. Med. Chem., 34, 447, (1991), carbonyldiimimidazole (CDI) and dicyclohexylcarbodiimide, optionally in the presence of a catalyst such as dimethylaminopyridine (DMAP) or 4-pyrrolidinopyridine. Suitable solvents include dimethylacetamide, dichloromethane, benzene, tetrahydrofuran, and dimethylformamide. The coupling reaction can be conducted in a temperature range of about −40° to 40° C.

In a further aspect, the present invention provides stereoselective methods of preparing (S) enantiomer intermediates useful in the synthesis of (S)-(−)-N-(4-benzoylphenyl)-3,3,3-trifluoro-2-hydroxy-2-methylpropanamide and other N-aryl or -pyridylpropanamides disclosed in U.S. Pat. No. 5,272,163. (S) Enantiomer intermediates allow (S)-(−)-N-(4-benzoylphenyl)-3,3,3-trifluoro-2-hydroxy-2-methylpropanamide or other N-aryl or -pyridylpropanamide of Formula I to be prepared without the tedious stereoselective salt formation steps using resolving agents such as α-methylbenzylamine or norephedrine. The present invention provides stereoselective processes, each containing an enzymatic step, for preparing (S)-3,3,3-trifluoro-2-hydroxy-2-methylpropanenitrile and (S)-3,3,3-trifluoro-2-hydroxy-2-methylpropanoic acid.

In the first stereoselective process for preparing such intermediates, (S)-3,3,3-trifluoro-2-hydroxy-2-methylpropanoic acid is prepared by selective cleavage of an ester of racemic 3,3,3-trifluoro-2-hydroxy-2-methylpropanoic acid using a hydrolase, preferably a lipase such a s Candida antarctica lipase. The method comprises treating an ester of 3,3,3-trifluoro-2-hydroxy-2-methylpropanoic acid which preferably has the Formula V:

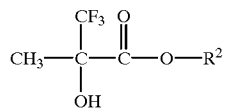

Formula V wherein $R^2$ is $C_1$–$C_6$ alkyl, $C_1$–$C_4$ alkoxy, or phenyl, with a hydrolase enzyme. The ester can be prepared using conventional methods, such as preparation from the racemic acid with a mineral acid and the appropriate alcohol. For example, the propyl and butyl esters can be prepared by reacting racemic 3,3,3-trifluoro-2-hydroxy-2-methylpropanoic acid and propanol or butanol in the presence of a small amount of concentrated sulfuric acid or dry hydrogen chloride to form the respective propyl or butyl ester. The ester of Formula V can also be prepared by hydrolysis of racemic 3,3,3-trifluoro-2-hydroxy-2-methylpropanenitrile with sulphuric acid in the presence of the appropriate alcohol.

The ester of Formula V is selectively cleaved by a hydrolase enzyme, preferably a lipase such as Candida antarctica lipase, to form a product mixture of ester and acid. The reaction with the hydrolase enzyme is preferably carried out in an aqueous buffer solution at a pH acceptable for the enzyme employed to provide a good rate of reaction, usually between about pH 5 and about pH 9. Cosolvents such as methyl-tert butyl ether (MTBE) can also be used. The reaction is allowed to proceed until a satisfactory amount of the ester has reacted, usually after about one to three days. The actual reaction time will depend on factors such as the enzyme, substrate and solvents used. The ester and acid can then separated using chromatography on silica gel or any other appropriate method known in the art. Depending on the selectivity of the enzyme, the desired (S) enantiomer may be present as the recovered unreacted ester or as the free acid. In the case where the unreacted ester contains the (S) enantiomer, the ester group can then be removed to generate the (S)-3,3,3-trifluoro-2-hydroxy-2-methylpropanoic acid by reaction with a base such as sodium hydroxide, followed by neutralization.

To prepare (S)-(−)-N-(4-benzoylphenyl)-3,3,3-trifluoro-2-hydroxy-2-methylpropanamide, the (S)-3,3,3-trifluoro-2-hydroxy-2-methylpropanoic acid is then reacted with 4-aminobenzophenone in accordance with the methods herein. Other N-aryl or -pyridyl-propanamides of Formula I can be prepared using the (S)-3,3,3-trifluoro-2-hydroxy-2-methylpropanoic acid and substituting an amine of Formula IV for 4-aminobenzophenone in the synthesis shown in Scheme 2, as described herein.

The compounds of Formula V

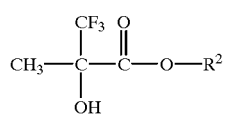

Formula V wherein $R^2$ is $C_3$–$C_6$ alkyl, $C_1$–$C_4$ alkoxy, or phenyl, form another aspect of the invention.

The compounds of Formula VI

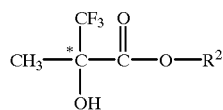

Formula VI wherein * is an optically active chiral center and $R^2$ is $C_2$–$C_6$ alkyl, $C_1$–$C_4$ alkoxy, or phenyl form a further aspect of the invention. Preferably, * is an optically active chiral center having the (S) configuration.

In the second stereoselective method for preparing such intermediates, (S)-3,3,3-trifluoro-2-hydroxy-2-methylpropanoic acid is prepared by treating or reacting a compound of Formula VII,

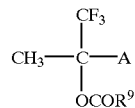

Formula VII wherein A is CN, COH, $CH(OR^3)_2$, $COR^4$, $COOR^5$, $CONH_2$, $CONHR^6$ or $CONR^7R^8$; $R^3$, $R^4$, $R^5$, $R^6$, $R^7$ and $R^8$ are independently selected from alkyl, aryl, and aralkyl; and $R^9$ is alkyl, aryl or aralkyl, any of which may be optionally independently substituted with substituents selected from a hydroxy, halogen, $C_1$–$C_4$ alkoxy, cyano, $C_1$–$C_4$ alkylamino or $C_1$–$C_4$ dialkylamino, with a hydrolase enzyme, preferably a lipase such as crude porcine pancreatic lipase, which selectively cleaves the ester group to provide the corresponding alcohol of Formula VIII

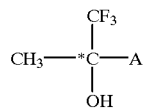

Formula VIII wherein * is an optically active chiral center and A has the meaning previously defined herein, and converting the A group of the compound of Formula VIII to an acid (i.e., a COOH group). $R^9$ is preferably optionally substituted $C_1$–$C_{10}$ alkyl, more preferably $C_1$–$C_5$ alkyl. A is preferably CN. Preferably, $R^3$, $R^4$, $R^5$, $R^6$, $R^7$ and $R^8$ are independently $C_1$–$C_{10}$ alkyl, more preferably $C_1$–C5 alkyl.

The reaction with the hydrolase may be carried out in an aqueous buffer, with the pH of the solution adjusted to an acceptable value for the enzyme employed, generally between about pH 7 and about pH 7.5. Cosolvents such as MTBE can also be used. The reaction is allowed to proceed until a satisfactory amount of the ester has reacted. The reaction is usually allowed to proceed for about three days, but the actual time will depend on factors such as the enzyme, substrate and solvents used.

The mixture of alcohol and ester may then be separated by conventional methods such as chromatography on a silica column. Depending on the selectivity of the enzyme, the desired (S) enantiomer may be present as the recovered (unreacted) ester or the alcohol. Where the desired (S) enantiomer is the recovered ester, the ester can then be treated with a base such as sodium hydroxide to remove the ester group. The A group is converted to a carboxyl group by standard methods to provide (S)-3,3,3-trifluoro-2-hydroxy-2-methylpropanoic acid. Optionally, depending on the nature of A, the ester removal and nitrile hydrolysis steps may be combined.

In a preferred embodiment, (S)-3,3,3-trifluoro-2-hydroxy-2-methylpropanoic acid is prepared by reaction of (S)-3,3,3-trifluoro-2-hydroxy-2-methylpropanenitrile with acid. (S)-3,3,3-Trifluoro-2-hydroxy-2-methylpropanenitrile can be prepared by reacting 1,1,1-trifluoroacetone with sodium cyanide in the presence of hydrochloric acid to form racemic 3,3,3-trifluoro-2-hydroxy-2-methylpropanenitrile. The racemic 3,3,3-trifluoro-2-hydroxy-2-methylpropanenitrile is then reacted with an acid chloride such as butyryl chloride to form the ester. The racemic ester is reacted with a lipase enzyme such as crude porcine pancreatic lipase that selectively cleaves the ester group from the (R) enantiomer leaving the ester of the (S) enantiomer. The ester group of the (S) enantiomer is then removed using standard procedures to provide (S)-3,3,3-trifluoro-2-hydroxy-2-methylpropanenitrile, which is in turn treated with acid such as sulfuric acid or hydrochloric acid to form (S)-3,3,3-trifluoro-2-hydroxy-2-methylpropanoic acid.

A further aspect of the invention provides a method of preparing (S)-3,3,3-trifluoro-2-hydroxy-2-methylpropanenitrile, which method comprises treating a compound of Formula VII wherein A is CN with a hydrolase enzyme preferably a lipase such as crude porcine pancreatic lipase.

The present invention thus also provides compounds of Formula VII

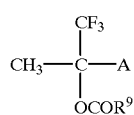

Formula VII wherein A and $R^9$ have the meanings previously defined herein; and compounds of Formula IX

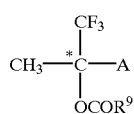

Formula IX wherein * is an optically active chiral center and A and $R^9$ have the meanings previously defined herein. Preferably, * denotes an optically active chiral center having the (S) configuration.

The present invention also provides compounds of Formula VIII

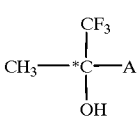

Formula VIII wherein * is an optically active chiral center and A has the meaning previously defined herein. Preferably, * denotes an optically active chiral center having the (S) configuration.

The enzymatic step of the methods described herein can be performed using any type of hydrolase enzyme that is capable of selectively cleaving an ester group to form an alcohol, such as a lipase, esterase, peptidase or protease. The enzyme may be obtained from microbial culture or from plants or animals. Such enzymes are commercially available or can be prepared by methods known in the art. It has been found that lipase enzymes can selectively cleave esters formed from N-(4-benzoylphenyl)-3,3,3-trifluoro-2-hydroxy-2-methylpropanamide and other esters described herein to effect resolution of the enantiomers in acceptable yield. It has been found that commercially available lipase preparations preferentially cleave the ester group from the (R) enantiomer, leaving the (S) enantiomer in ester form. A preferred lipase is crude porcine pancreatic lipase which is readily available commercially. Lipase from other species can also be used. Porcine pancreatic lipase provides good specificity and rate of reaction. The enzymes useful in the present invention are commercially available and can be used in the reaction mixture as received with no further treatment or the enzymes can be prior treated, for example, by dissolving in buffer at around pH 7 to 7.5, and adsorbing onto a support such as glass beads, diatomaceous earth, charcoal, ion exchange resins or silica gel or covalently binding to a polymeric support.

Typically, the enzymatic step of the methods of the present invention can be performed with from 1:10 to 100:1 (weight:weight) substrate:enzyme ratio. Substrate:enzyme ratios of from 5:1 to 1:1 have been found to provide satisfactory results. The ratio of substrate to enzyme may need to be varied to produce a satisfactory rate of reaction depending on such factors as starting materials, the enzyme used and reaction conditions such as temperature and solvent. The enzymatic reaction is allowed to proceed until satisfactory amounts of the alcohol are formed by the cleavage of the ester group from the starting materials. Generally, the enzymatic reaction will be allowed to proceed for about twelve hours to about four or five days, preferably from about one to three days.

The pH of the reaction mixture is generally from about 5 to about 9, preferably from about 7 to about 8. The enzymatic step is generally performed at a temperature from about 15 to about 40° C., preferably from about 25 to about 38° C. The reaction conditions may need to be varied within (or even outside) the aforementioned ranges to provide a satisfactory rate of reaction depending on such factors as starting materials, enzyme and solvent employed.

The solvent and any cosolvent used in the reaction mixture will vary depending on such factors as the enzyme and substrate employed in the reaction. The solvent may also influence the selectivity and/or rate of the enzymatic reaction and in such cases the solvent can be selected to increase the rate of reaction (in relation to other solvents) and/or influence the selectivity of the enzyme for the desired enantiomer. The reaction mixture solvent may be any conventional aqueous buffer such as potassium dihydrogen phosphate buffer. Suitable cosolvents for the reaction include MTBE.

The enzymatic resolution reaction has been taken almost to completion (i.e., reaction of almost all of the (R) ester) in two days using a substrate:enzyme ratio of 1:1 wt/wt with the racemic ester derived from N-(4-benzoylphenyl)-3,3,3-trifluoro-2-hydroxy-2-methylpropanamide and butyric acid and crude porcine pancreatic lipase. A substrate:enzyme ratio of 5:1 wt/wt of the same materials produced approximately 25% hydrolysis of the ester in two days. The reaction of porcine pancreatic lipase with racemic ester derived from N-(4-benzoylphenyl)-3,3,3-trifluoro-2-hydroxy-2-methylpropanamide and butyric acid, after hydrolyzing recovered ester, provided an enantiomeric excess of 98.5% (S) isomer in 35% yield (70% of the available (S) ester).

As used herein, alkyl and the alkyl portions of alkoxy and aralkyl include both straight and branched chain radicals.

Particular values of alkyl include methyl, ethyl, propyl, butyl, pentyl, hexyl, heptyl, octyl, isopropyl, sec-butyl and tert-butyl.

Particular values of alkoxy include methoxy, ethoxy, propoxy, and butoxy.

Particular values of aralkyl include benzyl, phenylethyl, and phenylpropyl.

Particular values of aryl include phenyl.

Particular values of alkylamino include methylamino, ethylamino, propylamino and butylamino.

Particular values of dialkylamino include dimethylamino and diethylamino.

Particular values of Ar as a six-membered heteroaryl ring containing 1–2 nitrogen atoms include 2-,3-, and 4-pyridyl, 2-pyrazinyl, 2- and 4-pyrimidinyl and 3- and 4-pyridazinyl.

Particular values of Ar as a five-membered heteroaryl ring containing from 1–2 heteroatoms selected from nitrogen, oxygen and sulfur include 3, 4- and 5-isothiazolyl, 2-, 4- and 5-oxazolyl, 2, 4- and 5-thiazolyl, 2- and 3-furyl, and 2- and 3-furyl.

The term halogen refers to fluoro, chloro, bromo and iodo unless noted otherwise.

* denotes an optically active chiral center in the R or S configuration.

The invention is further illustrated by reference to the following examples which do not limit the scope of the invention.

EXAMPLES

Example 1

Synthesis of (S)-(–)-N-(4-benzoylphenyl)-3,3,3-trifluoro-2-hydroxy-2-methylpropanamide A. Preparation of Racemic Butyric Ester Derived from N-(4-benzoylphenyl)-3,3,3-trinfluoro-2-hydroxy-2-methylpropanamide.

Racemic N-(4-benzoylphenyl)-3,3,3-trifluoro-2-hydroxy-2-methylpropanamide (25 g) and triethylamine (15 ml) were stirred in acetonitrile (150 ml) at 0–5° C. and butyryl chloride (10 ml) was added over 15 min. at <10° C. After 2 hr. 45 min. at <10° C., further triethylamine (2 ml) and butyryl chloride (1 ml) were added and the reaction was stirred at 20° C. for 1 hr. 30 min. when further butyryl chloride (1 ml) was added. The reaction was complete after a further 30 min. Water (450 ml) then ethyl acetate (175 ml) were added, the mixture was stirred for 15 min. then separated. The aqueous layer was re-extracted with ethyl acetate (175 ml), then the combined organic extracts washed with 50% brine (150 ml), filtered and evaporated. The oil was crystallized by dissolving in hot tert-butyl methyl ether (MTBE)(60 ml), slowly adding hexane (400 ml) over 10 min. then cooling to 5° C. over 1 hr. After 30 min. at 5° C., the racemic butryic ester derived from N-(4-benzoylphenyl) 3,3,3-trifluoro-2-hydroxy-2-methylpropanamide was filtered off, washed with hexane (50 ml) and dried in vacuo at 40° C. Yield: 26 g (86%)

B. Enzymatic Hydrolysis of the Butyric Ester Derived from N-(4-benzoylphenyl)-3,3,3-trifluoro-2-hydroxy-2-methylpropanamide 5 Millimolar potassium dihydrogen phosphate solution (50 ml) was adjusted to pH 7.1 with 0.1N sodium hydroxide solution (2 ml), porcine pancreatic lipase (Biocatalysts, Treforest, UK) (0.2 g) added and the pH again adjusted to 7.1 with 0.1N sodium hydroxide solution (2 ml). Racemic butyric ester derived from N-(4-benzoylphenyl)-3,3,3-trifluoro-2-hydroxy-2-methylpropanamide (1 g) was dissolved in MTBE (10 ml) and added to the reaction, washing in with further MTBE (2 ml). The reaction was stirred at 38° C. under pH control initially set at 7.05 max/7.00 min. After 24 hr., further porcine pancreatic lipase (0.8 g) was added and the pH adjusted to 7.55 max/7.50 min and left for a further 42 hours when a total of 10 ml of 0.1 N sodium hydroxide had been added. The reaction mixture was acidified to pH 3.5 with 2 N HCl (2 ml), stirred for 15 min., then ethyl acetate (30 ml) was added and the mixture was stirred for a further 10 min. The mixture was then filtered and the residue washed with ethyl acetate (20 ml). The aqueous phase was separated and extracted with ethyl acetate (30 ml). The combined organic extracts were washed with 50% brine (20 ml), filtered and evaporated to an oil which partly crystallized. Yield: 0.95 g. The product was a mixture of the (R)-alcohol (99% enantiomeric excess) and ester.

Separation of Product

The product was separated by flash column chromatography using Silica Gel 60 (Fluka, Buchs, Switzerland) eluting with 5% ethyl acetate/toluene to remove the ester, then with 50% ethyl acetate/toluene to remove the alcohol. Alcohol yield: 338 mg; (R)-enantiomer with 97.6% enantiomeric excess. Ester yield: 415 mg.

C. Hydrolysis of the Recovered Ester

The recovered ester (415 mg) was dissolved in methanol (25 ml), 100° TW sodium hydroxide solution added and stirred for 30 min. at 20° C. Water (70 ml) was added, the mixture was acidified to pH 2 with 2N HCl (2 ml) and then extracted with ethyl acetate (2×30 ml). The organic extracts were washed with 50% brine (20 ml), filtered and evaporated to a white solid. Yield of (S)-(–)-N-(4-benzoylphenyl)-3,3,3-trifluoro-2-hydroxy-2-methylpropanamide: 297 mg (71.7%, 98.5% enantiomeric excess).

Example 2

Effect of Acid Moiety on Rate of Hydrolysis of Ester and Specificity of Reaction.

A range of esters was prepared from racemic N-(4-benzoylphenyl)-3,3,3-trifluoro-2-hydroxy-2-methylpropanamide and the corresponding acid chlorides. These were subjected to cleavage by porcine pancreatic lipase and analyzed after 24 hr.

Phosphate buffer (50 ml) was adjusted to pH 7.6 at 38° C., enzyme (0.2 g) was added and the pH readjusted to 7.6. The racemic ester derived from N-(4-benzoylphenyl)-3,3,3-trifluoro-2-hydroxy-2-methylpropanamide (1.0 g) in MTBE was added, followed by an MTBE wash (total 12 ml), and the mixture was then stirred at approximately 38° C. under pH control using an autotitrator and 0.1 N NaOH. At the end of the reaction, the pH of the mixture was adjusted to <5 with 2N HCl and the product extracted into ethyl acetate. The ester and alcohol may be separated by chromatography and the recovered ester hydrolyzed using NaOH in methanol. The (R) and (S) alcohols were analyzed by high pressure liquid chromatography (HPLC) using a Chiracel OJ (Daicel Chemical Industries) column to determine the enantiomeric purity.

The degree of conversion was determined along with the enantiomeric excess of the (R) alcohol product after this had been separated from unreacted ester, except for the benzoate and phenyl acetate reactions which were extremely slow. Results are shown in Table 1:

TABLE 1

| Ester | Conversion after 24 hr. using 1:5 w/w enzyme:ester | Selectivity ee (enantiomeric excess) of (R) isomer product |
|---|---|---|
| Acetate | 2.5% | 86% ee |
| Propionate | 6% | 87% ee |
| Butyrate | 10% | 99% ee |
| Hexanoate | 4.7% | 98% ee |
| Benzoate | <1% | N/A |
| Phenylacetate | <1% | N/A |
| Monochloroacetate | approx. 65% | approx. 30% ee |

The monochloroacetate was hydrolyzed substantially faster than any of the other esters tested; this reaction had continued well beyond the 50% mark and there was no detectable (R) isomer in the (S)-(−)-N-(4-benzoylphenyl)-3,3,3-trifluoro-2-hydroxy-2-methylpropanamide recovered from the residual ester indicating good selectivity.

Example 3

Hydrolysis of Racemic Ester Formed From N-(4-benzoylphenyl)-3,3,3-trifluoro-2-hydroxy-2-methylpropanamide and Butyric Acid A. Racemic N-(4-benzoylphenyl)-3,3,3-trifluoro-2-hydroxy-2-methylpropanamide was prepared from racemic 3,3,3-trifluoro-2-hydroxy-2-methylpropanoic acid and 4-aminobenzophenone in accordance with Scheme 2 and converted to the butyric ester. The butyric ester was screened against a range of esterases and lipases. Racemic butyric ester of N-(4-benzoylphenyl)-3,3,3-trifluoro-2-hydroxy-2-methylpropanamide (0.5 g) in DMSO (0.3 ml) was added to the enzyme (0.1 g) in buffer maintained at pH 7.5 at 30° C. The results are shown in Table 2.

TABLE 2

| Enzyme | Extent of Reaction | Ratio (S):(R) of Product Alcohol |
|---|---|---|
| Chirazyme L5 (Boehringer) (lipase) | <20% | 1:1 |
| Sheep liver acetone powder (Sigma) | <2% | 2:1 |
| Pig liver acetone powder (Sigma) | <2% | 1.1.3 |
| Pancreatic lipase (Biocatalysts) | <10% | 1:10 |
| Chirazyme L7 (Boehringer) (lipase) | <10% | 1:3.6 |
| Pancreatic lipase (Fluka) | <5% | 1:15.6 |

B. Racemic N-(4-benzoylphenyl)-3,3,3-trifluoro-2-hydroxy-2-methylpropanamide was prepared from racemic 3,3,3-trifluoro-2-hydroxy-2-methylpropanoic acid and 4-aminobenzophenone in accordance with Scheme 2 and converted to the butyric ester. The butyric ester was hydrolyzed using porcine pancreatic lipase (Biocatalysts). Racemic butyric ester of N-(4-benzoylphenyl)-3,3,3-trifluoro-2-hydroxy-2-methylpropanamide (0.5 g) in MTBE (5 ml) was added to the enzyme (0.1 g) in buffer maintained at pH 7.5 at 30° C. Using porcine pancreatic lipase, the reaction proceeded to approximately 25% conversion in two days and showed very little hydrolysis of the desired (S) enantiomer. Adding more porcine pancreatic lipase (0.2 g) gave 35% reaction after a further three hours and work-up gave the (R) alcohol with an enantiomeric excess of approximately 99%. The product was chromatographed to give (R) alcohol of 99% enantiomeric excess, with the recovered ester after hydrolysis having an enantiomeric excess of 50%.

The reaction was taken to almost completion in two days using 1:1 (w/w) enzyme:substrate to give (S)-(−)-N-(4-benzoylphenyl)-3,3,3-trifluoro-2-hydroxy-2-methylpropanamide after hydrolyzing recovered ester, with an enantiomeric excess of 98.5% in 35% yield based on input racemic butyric ester of N-(4-benzoylphenyl)-3,3,3-trifluoro-2-hydroxy-2-methylpropanamide (i.e., 70% of available (S) ester).

Example 4

Enzymatic resolution of esters of 3,3,3-trifluoro-2-hydroxy-2-methylpropanoic Acid The reactions were carried out at 38° C. using a pH controller set at 7.10 max/7.07 min. 5 Millimolar potassium dihydrogen phosphate solution (100 ml) and the immobilised Candida antarctia lipase (Novozyme® SP435, Boehringer Mannhein) (2 g) were stirred together and the pH was adjusted to 7.1 with 0.5N aqueous sodium hydroxide solution (2 ml) at 38° C. The racemic methyl, ethyl, or butyl ester of 3,3,3-trifluoro-2-hydroxy-2-methylpropanoic acid (5 g), optionally dissolved in methyl tert-butyl ether (MTBE) (50 ml) or tert-butanol (50 ml), was added. The reaction mixture was stirred until an amount of 0.5N sodium hydroxide solution had been added which corresponded to approx. 50% hydrolysis. Optionally, more of the enzyme may be added to increase the rate of the hydrolysis.

Further MTBE (50 ml) was added, the reaction mixture was stirred for 15 minutes then filtered, and the residue was washed with MTBE (15 ml). The aqueous layer was separated and extracted with MTBE (30 ml). The combined organic extracts were washed with brine (30 ml) then filtered and evaporated to yield the unreacted ester. The enantiomeric ratio of the ester may be determined by NMR analysis using a chiral shift reagent such as 2,2,2-trifluoro-1-(9-anthryl)ethanol (tfae). The aqueous layer from the separation was acidified to about pH 2 and extracted with either MTBE or ethyl acetate (2×50 ml). The organic extracts were filtered through diatomaceous earth (2 g), washed with brine, filtered and evaporated to yield resolved 3,3,3-trifluoro-2-hydroxy-2-methylpropanoic acid which may be triturated with hexane before filtering off the solid. The enantiomeric purity of the acid may be determined by NMR in the presence of L-(−)-α-methylbenzylamine.

(i) The results of hydrolysis without co-solvent of the methyl, ethyl and butyl esters of 3,3,3-trifluoro-2-hydroxy-2-methylpropanoic acid are shown below in Table 3.

TABLE 3

| | Products (ee %) | |
|---|---|---|
| Ester | (R)-Acid | (S)-Ester |
| Methyl | 30 | — |
| Ethyl | 50 | 43 |
| Butyl | 67 | — |

(ii) The results of hydrolysis of the ethyl ester of 3,3,3-trifluoro-2-hydroxy-2-methylpropanoic acid with various co-solvents are shown below in Table 4.

TABLE 4

| Co-Solvent | Products (ee %) | |
|---|---|---|
| | (R)-Acid | (S)-Ester |
| Nil | 50 | 43 |
| MTBE | 60 | — |
| t-Butanol | 62 | — |

Example 5

Enzymatic resolution of esters of 3,3,3-Trifluoro-2-hydroxy-2-methylpropanoic Acid.

Example 5A

Reactions were performed either:
(a) in 7 ml glass vials containing 50 mM citric acid/sodium phosphate buffer, pH 7.6 (4 ml).

Ethyl ester of 3,3,3-trifluoro-2-hydroxy-2-methylpropanoic acid (40 mg) was suspended in the buffer and enzyme (10 mg) was added to start the reaction. The reactions were stirred gently at 22° C.
or
(b) in a 50 ml jacketed glass reaction vessel containing 5mM citric acid/sodium phosphate buffer, pH 7.6 (30 ml).

Ethyl ester of 3,3,3-trifluoro-2-hydroxy-2-methylpropanoic acid (300 mg) was suspended in the buffer and the pH readjusted to 7.6 using 0.1M sodium hydroxide solution. Enzyme (75 mg) was added to start the reaction. The reactions were stirred at 28° C. and the pH maintained at 7.6 by automatic titration with 0.1M sodium hydroxide solution.

Samples of the reaction mixtures (0.2 ml) were taken at intervals and extracted with hexane (1.8 ml). Samples were analyzed for extent of hydrolysis by measuring the concentration of residual ester by gas chromatography. Where reactions were carried out in the autotitrator the extent of hydrolysis could also be determined from consumption of sodium hydroxide solution.

The concentration of ester was determined by gas chromatography under the following conditions: chromatograph: Perkin Elmer 8500; column: DB5 (30 metre), J & W Scientific; oven: 120° C.; detector: 250° C.; injector: 250° C.; carrier gas: helium gas; pressure: 8 psi; detector: FID. The retention time for the ethyl ester was 2.8 minutes.

The enantiomeric excess of residual ester was also determined by gas chromatography under the following conditions: chromatograph: Perkin Elmer 8500;

column: CP Chirasil-Dex CB (25 metre), Chrompak; oven: temperature gradient isothermal 1–80° C. for 3 minutes, ramp –20° C./minute for 2 minutes, isothermal 2–120° C. for 6 minutes; other settings as for non-chiral analysis. Retention time for the (S)-enantiomer was 4.0 minutes and for the (R)-enantiomer was 4.1 minutes.

The results are shown in the Table 5. As shown in Table 5, hydrolysis of the ethyl ester of 3,3,3-trifluoro-2-hydroxy-2-methylpropanoic acid by *Aspergillus oryzae*, *Bacillus licheniformis*, *Aspergillus sojae* and SP539 enzymes provided good selectivity for the (R) enantiomer of the ethyl ester of 3,3,3-trifluoro-2-hydroxy-2-methylpropanoic acid.

Example 5B

The enzymes from *Aspergillus sojae* (Sigma) (protease) and SP539 (Novo) (protease) were also used to hydrolyze the butyl ester of 3,3,3-trifluoro-2-hydroxy-2-methylpropanoic acid. Analytical procedures were the same as those used for the ethyl ester in Example 5A. Retention time for the butyl ester was 4.6 minutes (DB5 column). Retention time for the (S)-enantiomer was 6.1 minutes. Retention time for the (R)-enantiomer was 6.3 minutes (CP Chirasil-Dex CB column).

Experiments were carried out in a pH autotitrator as described for the ethyl ester in Example 5A. Samples were taken over a time course. Results are shown in Tables 6 and 7.

TABLE 5

| Enzyme | Source | Reaction time (hours) | Hydrolysis (%) | Enantiomer excess of (S)-ester (%) |
|---|---|---|---|---|
| *Aspergillus oryzae* (protease) | Sigma | 48 | 62 | 75 |
| *Bacillus licheniformis* (protease) | Sigma | 2 | 68 | 80 |
| *Aspergillus sojae* (protease) | Sigma | 24 | 67 | 80 |
| SP539 (protease) | Novo | 0.25 | 67 | 90 |
| Chirazyme L2 (lipase) | Boehringer Mannheim | 24 | 50 | 49 |
| Chirazyme L6 (lipase) | Boehringer Mannheim | 24 | 64 | 32 |
| Horse liver acetone powder | Sigma | 1 | 53 | 39 |
| Amano N-conc (Rhizopus) (lipase) | Amano | 120 | 47 | 43 |

TABLE 6

*Aspergillus sojae* (Sigma)

| Reaction time (hours) | Hydrolysis (%) | Enantiomeric excess of (S)-ester (%) |
| --- | --- | --- |
| 5 | 74 | 53 |
| 21 | 90 | 87 |

TABLE 7

SP539 (Novo)

| Reaction time (hours) | Hydrolysis (%) | Enantiomeric excess of (S)-ester (%) |
| --- | --- | --- |
| 20 | 37 | 40 |
| 40 | 61 | 75 |
| 60 | 70 | 88 |
| 80 | 76 | 91 |
| 100 | 80 | 94 |

Example 6

Enzymatic Resolution of the Butyric Ester of 3,3,3-trifluoro-2-hydroxy-2-methylpropionitrile The reaction was carried out at 38° C. using a pH controller set at 7.50max/7.45 min. 5Millimolor potassium dihydrogen phosphate solution (100 ml) and crude porcine pancreatic lipase (PPL) (1 g) were stirred together and the pH adjusted to 7.5 with aqueous 0.1N sodium hydroxide solution (5 ml) at 38° C. Racemic butyric ester of 3,3,3-trifluoro-2-hydroxy-2-methylpropanenitrile (5 g), dissolved in MTBE (20 ml) was added, washing in with more MTBE (5 ml). After 7 hr further PPL (1 g) was added and the reaction was stirred overnight, when 30 ml of 0.1 n NaOH had been added. After a further 7 hr and a further 14 ml of 0.1N NaOH had been added, more PPL (2 g) was added, requiring 10 ml of 0.1N NaOH for neutralisation. The reaction was stirred for a further 2 days after which a further 69 ml of 0.1N NaOH had been added (a total of 113 ml consumed by the enzyme-catalysed hydrolysis versus a threoretical 119 ml).

MTBE (50 ml), diatomaceous earth (2 g) and 2N hydrochloric acid (5 ml) were added adjusting the ph to 5, the reaction mixture was stirred for 15 min then filtered. The aqueous layer was separated and extracted with MTBE (50 ml). The combined organic extracts were washed with 50% brine then filtered and evaporated. The resulting oil (3.3 g) was chromatographed on a silica gel flash column using dichloromethane as eluent. Unreacted ester (950 mg) was recovered and shown to be a single enantiomer by NMR in the presence of a shift agent.

The recovered ester (100 mg), water (1 ml) and concentrated hydrochloric acid (2 ml) were heated together at 100° C. for 6 hr then stirred at 20° C. overnight. Saturated brine (2 ml) was added and the mixture extracted with MTBE (2×5 ml). The MTBE solution was filtered and evaporated to yield an oil plus some solid which was triturated with hexane (2 ml). The solid (14.5 mg) was filtered off and washed with hexane (5 ml). NMR in the presence of L(−)-α-methylbenzylamine showed this to be the (S)-enantiomer of 3,3,3-trifluoro-2-hydroxy-2-methylpropanoic acid.

What is claimed is:

1. A method of preparing an optically active compound of Formula VIII

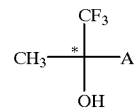

VIII where * is an optically active chiral center, comprising treating a racemic compound of Formula VII with a stereoselective hydrolase enzyme

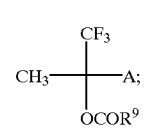

VII wherein:

$R^9$ is selected from $(C_1-C_{10})$alkyl, aryl and aryl$(C_1-C_3)$ alkyl, and each $R^9$ is substituted with 0, 1 or more substituents independently selected from hydroxy, halogen, $(C_1-C_4)$alkoxy, cyano, $(C_1-C_4)$alkylamino and $(C_1-C_4)$dialkylamino, and A is selected from CN, COH, CH$(OR^3)_2$, COR$^3$, COOR$^3$, CONH$_2$, CONHR$^3$ and CON$(R^3)_2$, wherein R$^3$, at each occurrence, is independently selected from $(C_1-C_{10})$ alkyl, aryl, and aryl$(C_1-C_3)$alkyl and each R$^3$ may be optionally substituted with substituents selected from hydroxy, halogen, $(C_1-C_4)$alkoxy, cyano, $(C_1-C_4)$ alkylamino and $(C_1-C_4)$dialkylamino, and isolating compound of Formula VIII.

2. The method of claim 1, further comprising a step of separating unhydrolyzed compound of Formula VII from compound of Formula VII.

3. The method of claim 2, further comprising a step of converting unhydrolyzed compound of Formula VII to a corresponding alcohol of Formula VIII.

4. The method of claim 1, wherein said stereoselective hydrolase enzyme is a lipase.

5. The method of claim 4, wherein said lipase is porcine pancreatic lipase.

6. The method of claim 4, wherein said lipase is *Candida antarctica* lipase.

7. The method of claim 1, wherein, in Formula VIII, A is CN.

* * * * *